(12) United States Patent
Williams

(10) Patent No.: US 11,116,697 B1
(45) Date of Patent: Sep. 14, 2021

(54) PRESCRIPTION ITEM DISPENSING DEVICE

(71) Applicant: Stan Williams, Birmingham, AL (US)

(72) Inventor: Stan Williams, Birmingham, AL (US)

( * ) Notice: Subject to any disclaimer, the term of this patent is extended or adjusted under 35 U.S.C. 154(b) by 0 days.

(21) Appl. No.: 16/942,396

(22) Filed: Jul. 29, 2020

(51) Int. Cl.
*A61J 7/00* (2006.01)
*A61J 1/03* (2006.01)
*A61B 5/1172* (2016.01)

(52) U.S. Cl.
CPC ............... *A61J 7/0076* (2013.01); *A61J 1/03* (2013.01); *A61B 5/1172* (2013.01)

(58) Field of Classification Search
CPC .......... A61J 7/0076; A61J 1/03; A61B 5/1172
USPC .................................................. 700/231–244
See application file for complete search history.

(56) References Cited

U.S. PATENT DOCUMENTS

| | | | |
|---|---|---|---|
| 5,213,232 A * | 5/1993 | Kraft | B65D 83/0409 198/657 |
| 6,529,446 B1 * | 3/2003 | de la Huerga | A61J 1/1437 368/10 |
| 6,633,796 B1 * | 10/2003 | Pool | A61J 7/0481 221/15 |
| 7,359,765 B2 | 4/2008 | Varvarelis | |
| 7,978,564 B2 | 7/2011 | De La Huerga | |
| 7,993,055 B2 * | 8/2011 | Nurse | G04C 11/00 368/277 |
| 8,384,517 B2 | 2/2013 | Chu | |
| 8,391,104 B2 | 3/2013 | de la Huerga | |
| 8,752,728 B2 * | 6/2014 | Tignanelli | B65D 83/0409 221/15 |
| 9,345,645 B1 * | 5/2016 | Chernyak | A61J 7/049 |
| 9,572,748 B2 | 2/2017 | Lim | |
| D799,060 S | 10/2017 | Ammar | |
| 9,870,450 B2 | 1/2018 | Blackburn | |
| 2017/0231870 A1 | 8/2017 | Stachler | |
| 2019/0307648 A1 * | 10/2019 | Bartos | A61J 7/0418 |

FOREIGN PATENT DOCUMENTS

WO     WO2014043054      3/2014

* cited by examiner

*Primary Examiner* — Michael Collins

(57) ABSTRACT

A prescription item dispensing device for regulated dispensing of controlled items includes an authenticator and a cap, with the latter being selectively lockable to a top of a tube. A mounting plate, which has an orifice positioned therein, is engaged to, and positioned within, the tube defining upper and lower chambers. The tube has an aperture positioned therein, which opens into the lower chamber. First and second doors, which are linear actuator actuated, are engaged to the tube and the mounting plate, respectively, to close the aperture and the orifice, respectively. A sleeve having a prescription item positioned therein is positioned in the upper chamber with a lower end of the sleeve aligned with the orifice. The authenticator authenticates an identity of a user, positioning the first and second doors for actuated opening to dispense a unit of the prescription item into the lower chamber for retrieval by the user.

19 Claims, 10 Drawing Sheets

PRESCRIPTION ITEM DISPENSING DEVICE

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

(g) BACKGROUND OF THE INVENTION

(1) Field of the Invention

The disclosure relates to dispensing devices and more particularly pertains to a new dispensing device for regulated dispensing of controlled items.

(2) Description of Related Art Including Information Disclosed Under 37 CFR 1.97 and 1.98

The prior art relates to dispensing devices. Prior art dispensing devices may comprise dispensers with bio-metric sensors or GPS transmitters, as well as lockable, monitored dispensers and dispensers that dispense according to a prescribed schedule and dosage amount.

(h) BRIEF SUMMARY OF THE INVENTION

An embodiment of the disclosure meets the needs presented above by generally comprising an authenticator and a cap, with the latter being selectively lockable to a top of a tube for closing the tube. A mounting plate, which has an orifice positioned therein, is engaged to, and positioned within, the tube defining upper and lower chambers. The tube has an aperture positioned therein, which opens into the lower chamber. First and second doors, which are selectively linear actuator actuated, are engaged to the tube and the mounting plate, respectively, and are configured to selectively close the aperture and the orifice, respectively.

A sleeve is selectively positionable in the upper chamber so that a lower end of the sleeve is aligned with the orifice. The sleeve is configured to position of a prescription item. The authenticator is engaged to the tube and is configured to authenticate an identity of a user, positioning the first and second doors for actuated opening to dispense a unit of the prescription item into the lower chamber for retrieval by the user via the aperture.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

Figure 13:
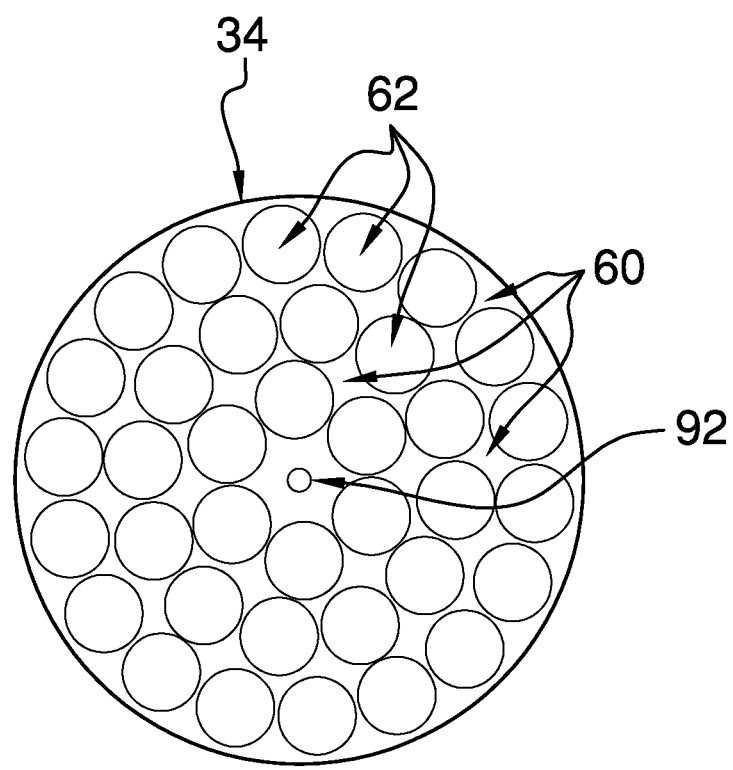

FIG. 13 a top view of a shell of an embodiment of the disclosure, wherein the shell has a plurality of panels positioned therein defining a plurality of compartments.

(j) DETAILED DESCRIPTION OF THE INVENTION

With reference now to the drawings, and in particular to FIGS. 1 through 13 thereof, a new dispensing device embodying the principles and concepts of an embodiment of the disclosure and generally designated by the reference numeral 10 will be described.

As best illustrated in FIGS. 1 through 13, the prescription item dispensing device 10 generally comprises an authenticator 12 and a cap 14, with the latter being selectively lockable to a top 16 of a tube 18 for closing the tube 18. A mounting plate 20, which has an orifice 22 positioned therein, is engaged to, and positioned within, the tube 18 defining upper 24 and lower 26 chambers. The tube 18 has an aperture 32 positioned therein, which opens into the lower chamber 26. First 28 and second 30 doors, which are selectively linear actuator actuated, are engaged to the tube 18 and the mounting plate 20, respectively, and are configured to selectively close the aperture 32 and the orifice 22, respectively.

A sleeve 34 is selectively positionable in the upper chamber 24 so that a lower end 36 of the sleeve 34 is aligned with the orifice 22. The sleeve 34 is configured for positioning of a prescription item. The authenticator 12 is engaged to the tube 18 and is configured to authenticate an identity of a user, positioning the first 28 and second 30 doors for actuated opening to dispense a unit of the prescription item into the lower chamber 26 for retrieval by the user via the aperture 32. An auger (not show) may be positioned in the sleeve 34 to facilitate dispensing of certain types of prescription items, such as leaf material.

A battery 38 and a microprocessor 40 are engaged to the tube 18 and are positioned in the lower chamber 26. The battery 38 is rechargeable. The microprocessor 40 is operationally engaged to the battery 38.

The cap 14 is threadedly couplable to the tube 18 and has a pinhole 42 extending thereinto proximate to a perimeter 44 thereof. A gasket 46 is engaged to the cap 14 and is configured to sealably engage the tube 18 as the cap 14 is threadedly engaged to the tube 18. A locking linear actuator 48 is positioned within a wall 50 of the tube 18 proximate to the top 16 and is operationally engaged to the microprocessor 40. The microprocessor 40 is positioned to selectively actuate the locking linear actuator 48 to insert a piston 52 of the locking linear actuator 48 into the pinhole 42, thereby preventing rotation of the cap 14 to lock the cap 14 to the tube 18.

Figure 1:
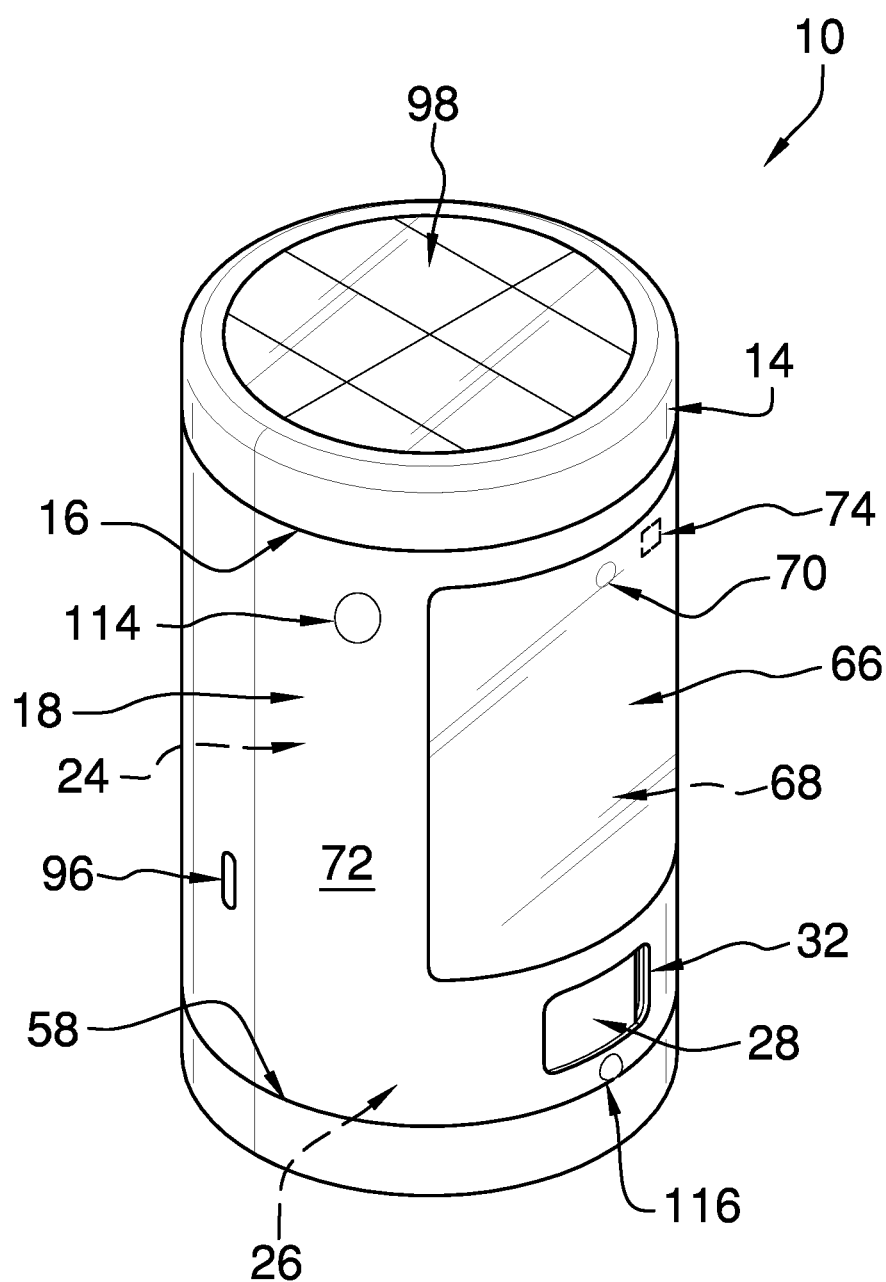
FIG. 1 is an isometric perspective view of a prescription item dispensing device according to an embodiment of the disclosure.
Figure 2:
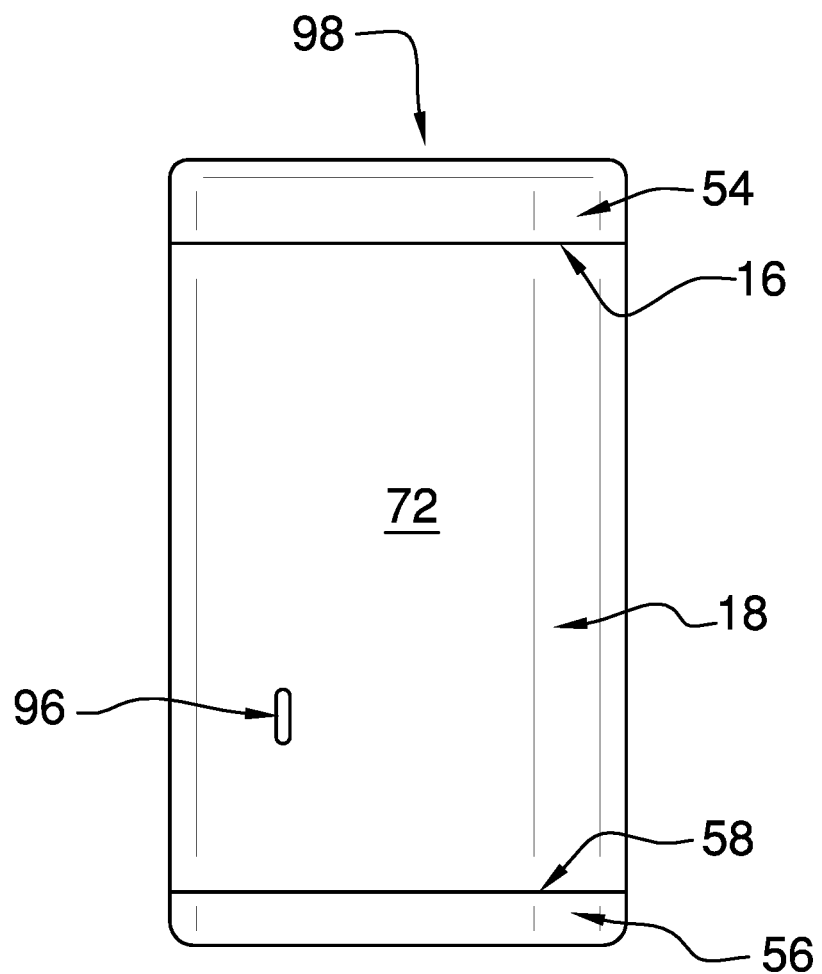
FIG. 2 is a side view of an embodiment of the disclosure.
Figure 3:
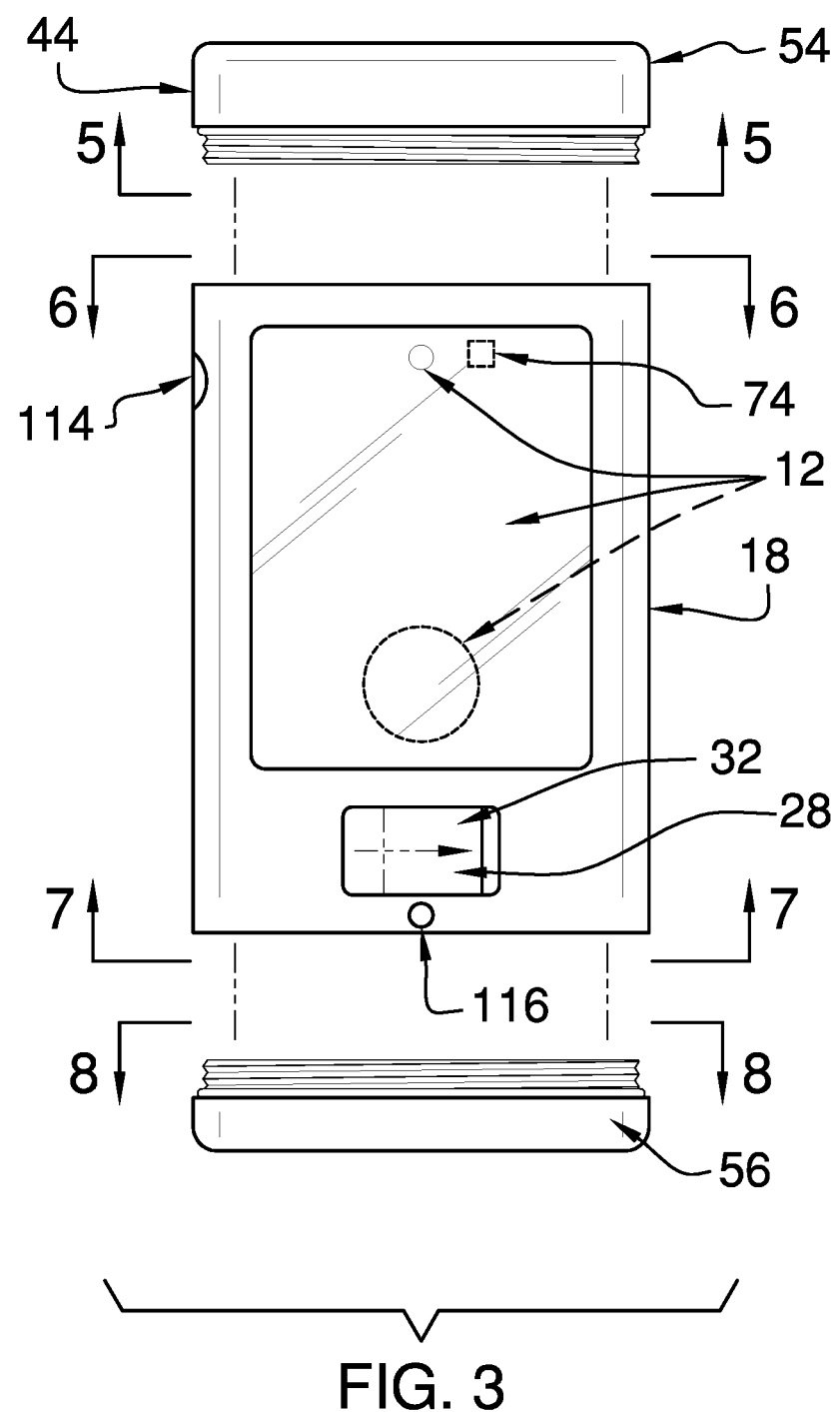
FIG. 3 is an exploded view of an embodiment of the disclosure.

The cap 14 may comprise an upper cap 54, which is selectively lockable to the top 16 of the tube 18, and a lower cap 56, which is selectively lockable to a bottom 58 of the tube 18, as shown in FIG. 3.

A plurality of panels 60 is engaged to and positioned in the sleeve 34. The panels 60 define a plurality of compartments 62 within the sleeve 34, with each compartment 62 having an associated opening 64 at the lower end 36 of the sleeve 34. As shown in FIG. 13, the panels 60 may define a plurality of compartments 62 that is configured for insertion of tubular items, such as preloaded syringes containing the prescription item.

Figure 11:
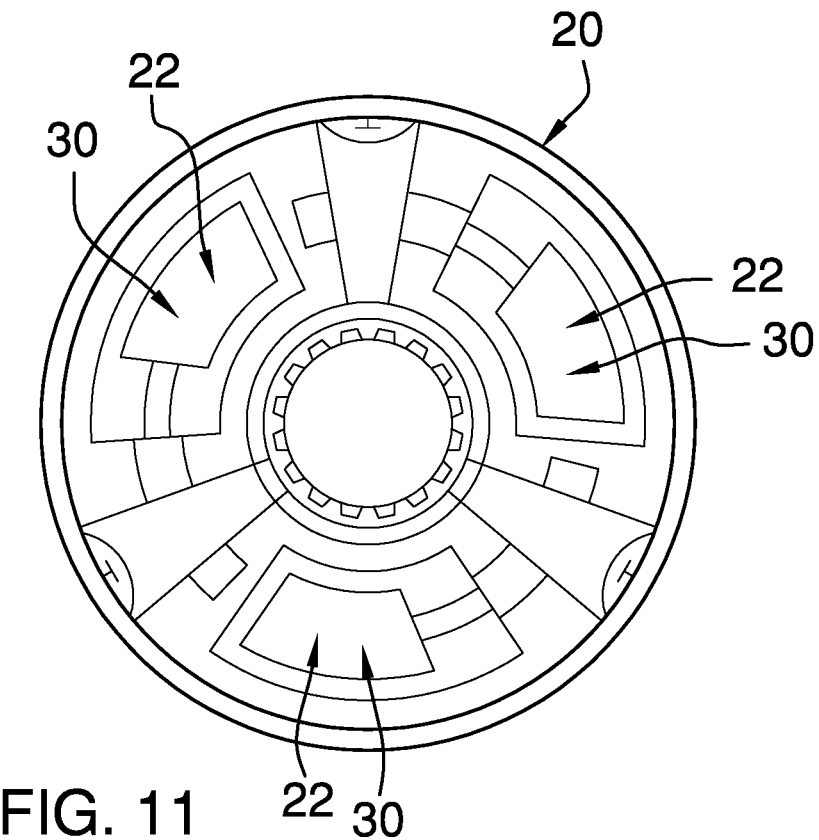
FIG. 11 is a top detail view of mounting plate of an embodiment of the disclosure.
Figure 12:
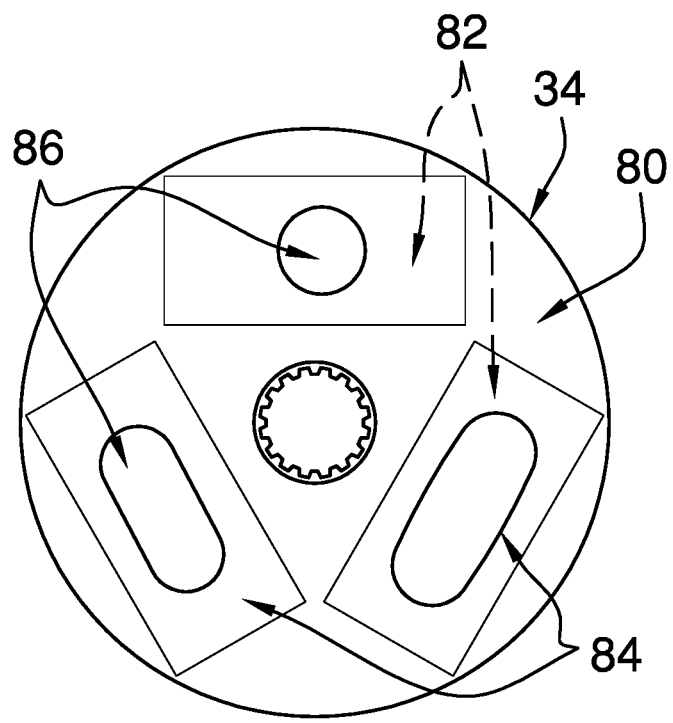
FIG. 12 is a bottom view of a sleeve of an embodiment of the disclosure.

The second door 30 is one of a set of second doors 30, with each second door 30 being positioned to selectively close an associated orifice 22 of a set of orifices 22. The associated orifice 22 is aligned with an opening 64 of a respective compartment 62 of the sleeve 34 that is positioned in the upper chamber 24. The set of second doors 30 comprises from one to six second doors 30, such as three second doors 30, as shown in FIGS. 11 and 13.

The authenticator 12 comprises at least one of a display 66, a fingerprint scanner 68, and a camera 70, which should be interpreted to mean only a display 66, only a fingerprint scanner 68, only a camera 70, or any combination thereof. The present invention also anticipates the authenticator 12 comprising other authenticating means, such as, but not limited to, voice recognition, retinal recognition, and the like.

Figure 4:
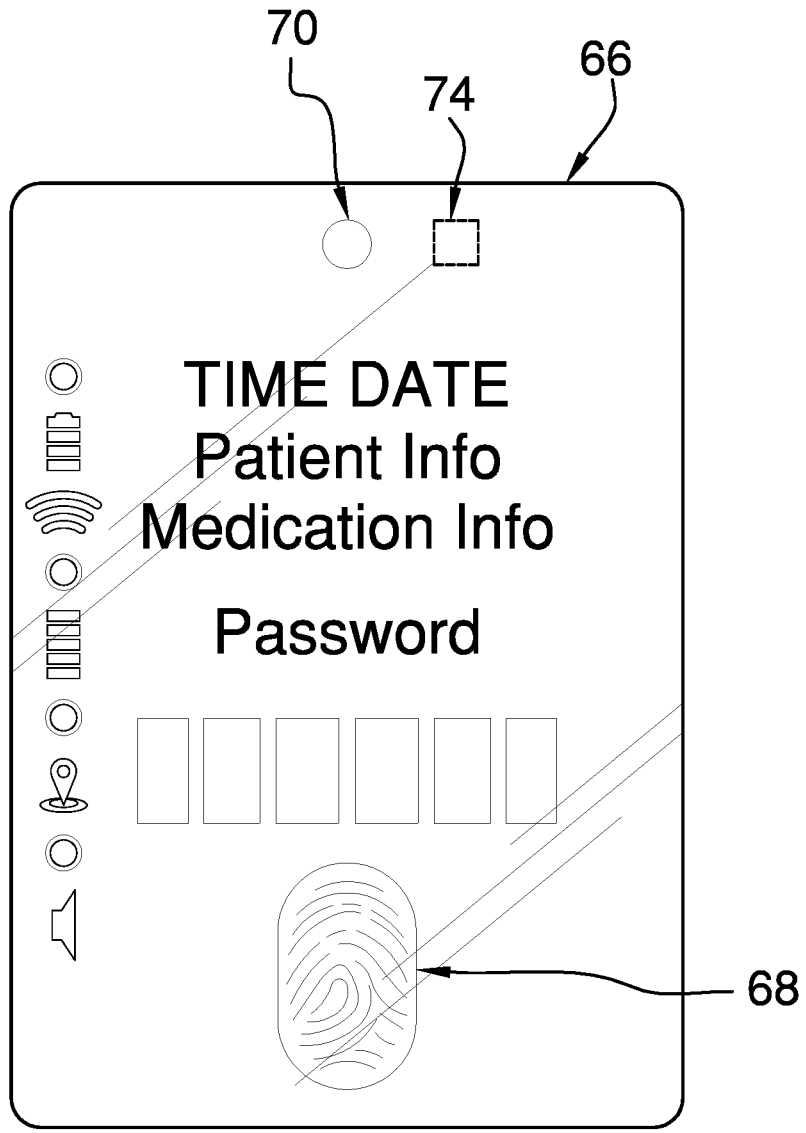
FIG. 4 is a detail view display of an embodiment of the disclosure.
Figure 5:
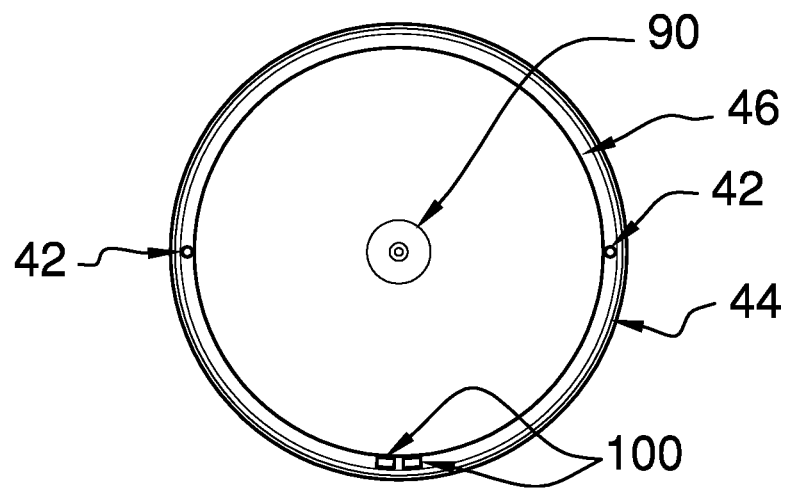
FIG. 5 is a bottom view of an upper cap an embodiment of the disclosure.
Figure 6:
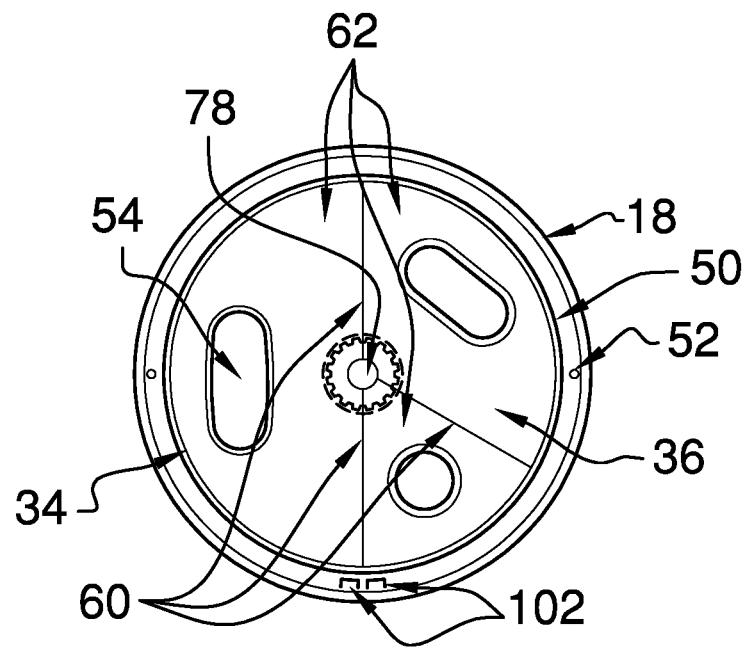
FIG. 6 is a top view of a tube of an embodiment of the disclosure with the upper cap removed and the sleeve positioned in the upper chamber.
Figure 7:
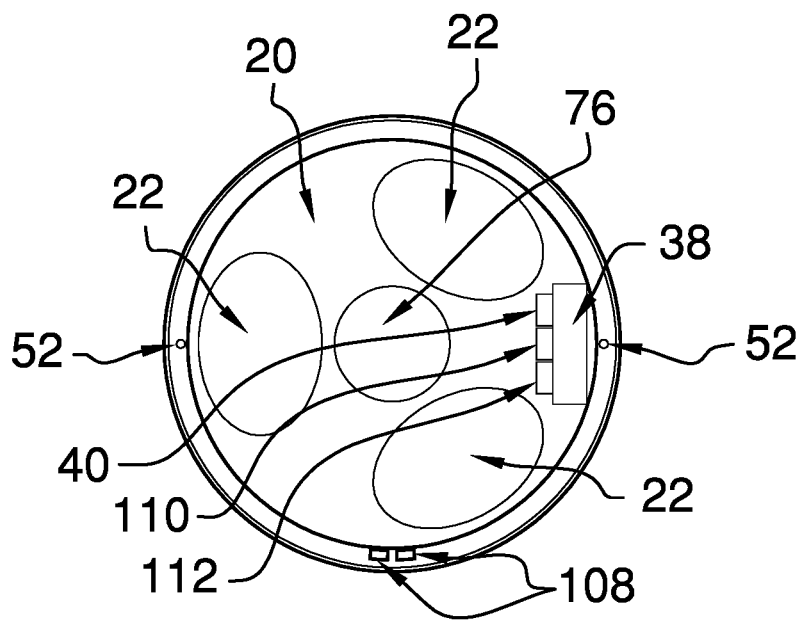
FIG. 7 is a bottom cross-sectional view of a tube of an embodiment of the disclosure.
Figure 8:
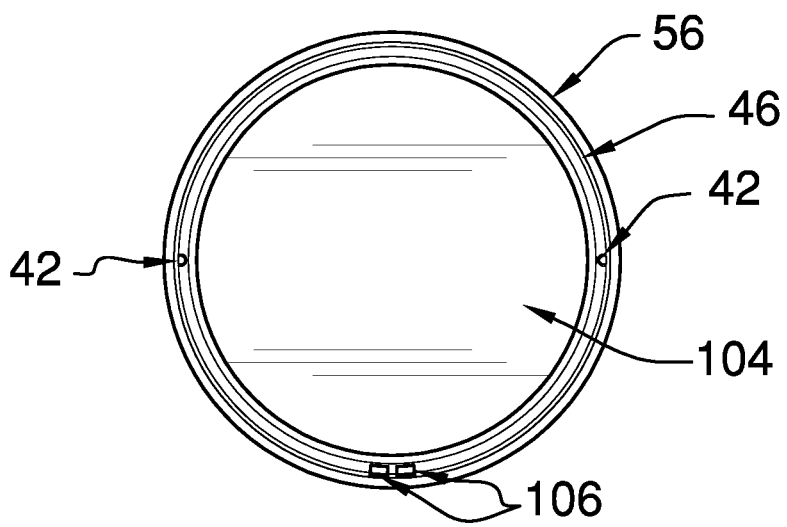
FIG. 8 is a top view of a lower cap an embodiment of the disclosure.
Figure 9:
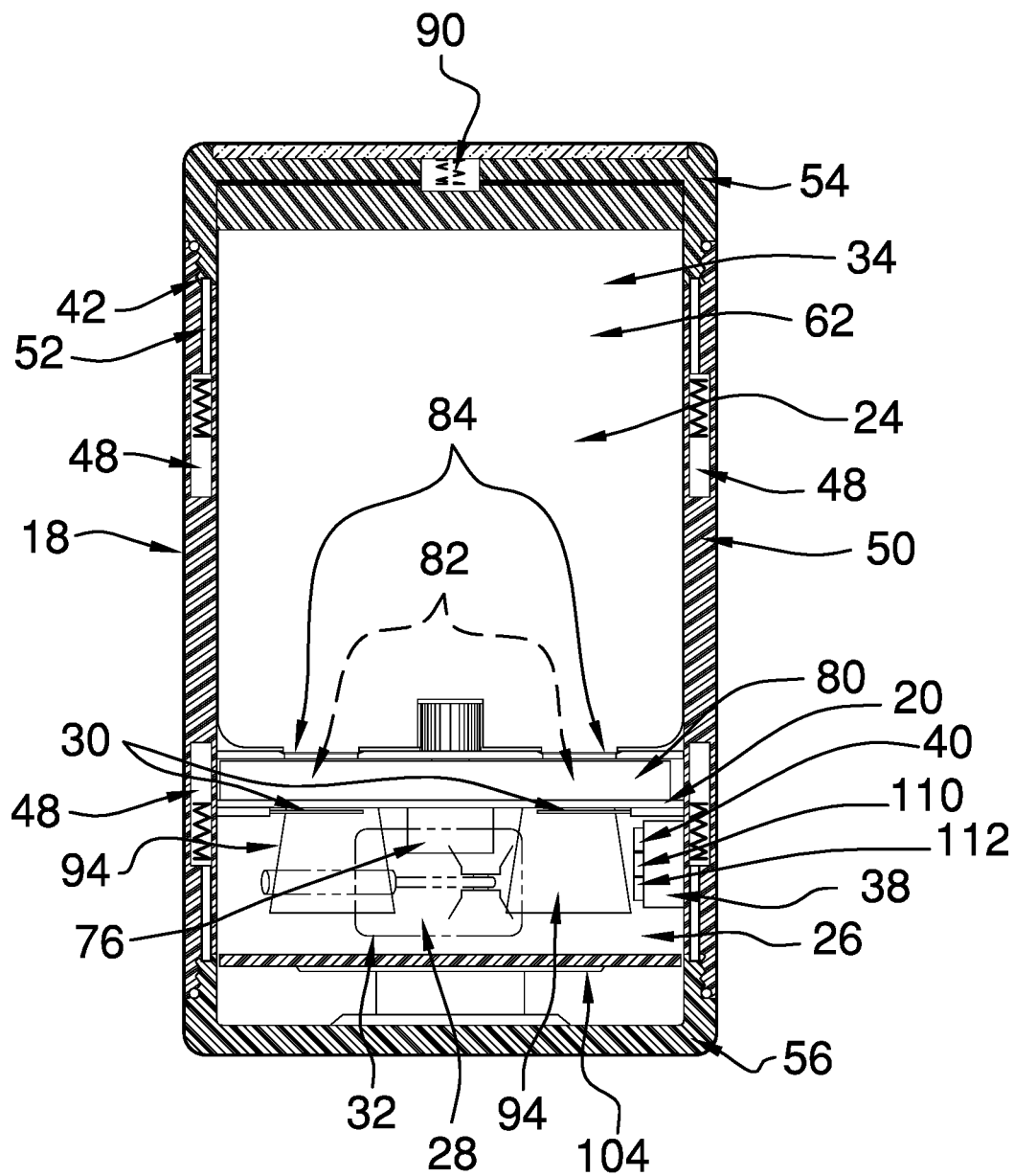
FIG. 9 is a side cross-sectional view of an embodiment of the disclosure.

The display 66 is engaged to an outer surface 72 of the tube 18 and is operationally engaged to the microprocessor 40. The display 66 is touch enabled and is configured to present a pin entry box. The microprocessor 40 is configured to verify the identity of the user or of a pharmacist upon successful entry of a pin code, for dispensing and filling purposes, respectively. The display 66 also may be configured to present one or more of a time, a date, user information, and prescription information, as shown in FIG. 4. The display 66 also may be configured to present other parameters, such as, but not limited to, battery life, charging indicators, signal strength, notification lights for indicating dosing time, and the like.

The fingerprint scanner 68 is engaged to the tube 18 and is operationally engaged to the microprocessor 40. The microprocessor 40 is configured to authenticate fingerprints to verify the identity of the user or the pharmacist. The fingerprint scanner 68 may be integral to the display 66.

The camera 70 is engaged to the outer surface 72 of the tube 18 and is operationally engaged to the microprocessor 40. The camera 70 is configured to capture a facial or ocular image of the user or the pharmacist, enabling the microprocessor 40 to perform facial or iris recognition, respectively, to verify the identity of the user or the pharmacist.

A sensor 74 is engaged to the outer surface 72 of the tube 18 and is operationally engaged to the microprocessor 40. The sensor 74 is configured to detect motion proximate to the tube 18 and to signal the microprocessor 40 thereof, positioning the microprocessor 40 to selectively actuate the display 66, the fingerprint scanner 68, and the camera 70.

A motor 76 is engaged to the mounting plate 20 and is operationally engaged to the microprocessor 40 so that the microprocessor 40 is positioned to selectively actuate the motor 76. The lower end 36 of the sleeve 34 is gearedly engageable to a shaft 78 of the motor 76. The motor 76 is positioned to rotate the sleeve 34 within the upper chamber 24 to selectively align a respective opening 64 with a respective orifice 22 in the mounting plate 20. Upon actuation of an associated second door 30, the unit of the prescription item can drop from the upper chamber 24 to the lower chamber 26.

Figure 10:
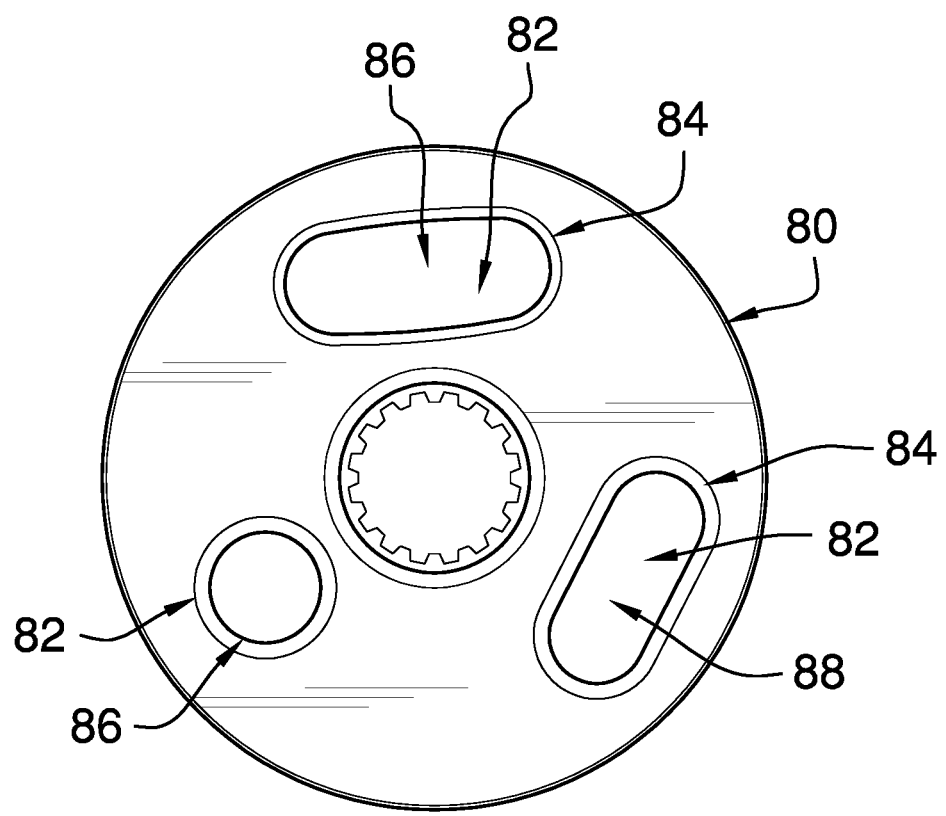
FIG. 10 is a detail view of pickup plate an embodiment of the disclosure.

A pickup plate 80 is selectively insertable into the upper chamber 24 and is gearedly engageable to the shaft 78 of the motor 76. The pickup plate 80 has a set of first voids 82 positioned therein. A plurality of inserts 84 is selectively engageable to the pickup plate 80 so that each first void 82 has a respective insert 84 positioned thereover. Each insert 84 has a second void 86 positioned therethrough, which has a respective profile 88 so that the plurality of inserts 84 comprises inserts 84 having second voids 86 of a variety of profiles 88. The second insert is selectively engageable to the pickup plate 80 to reprofile a respective second void 86 so that the respective second void 86 is configured for positioning of the unit of the prescription item. For example, the second void 86 may be reprofile to be circularly or ovally shaped, as shown in FIG. 10.

A spring bearing 90 is engaged to the cap 14. The shaft 78 of the motor 76 extends through a channel 92 in the sleeve 34, which is defined by the plurality of panels 60. The shaft 78 is positioned to engage the spring bearing 90, thus stabilizing the sleeve 34 within the upper chamber 24 and facilitating smooth rotation of the sleeve 34.

A chute 94 is engaged to the mounting plate 20 and extends from the orifice 22 into the lower chamber 26. The chute 94 is configured for direct the unit of the prescription item from the sleeve 34 into the lower chamber 26.

A port 96 is engaged to the outer surface 72 of the tube 18 and is operationally engaged to the battery 38 and the microprocessor 40. The port 96 is configured for insertion of a plug of a power cord (not shown) to operationally engage the battery 38 to a source of electrical current to charge the battery 38. The port 96 is configured for insertion of a plug of a communications cord (not shown) to operationally engage the microprocessor 40 to an electronic device to enable programming of the microprocessor 40, such as by a pharmacist entering a dispensing regimen.

A solar panel 98 is engaged to the upper cap 54 and is operationally engaged to the battery 38. The solar panel 98 is configured to convert electromagnetic radiation to an electrical current to charge the battery 38. A pair of first connectors 100 is engaged to the upper cap 54 and is operationally engaged to the solar panel 98. A pair of second connectors 102 is engaged to the tube 18 and is operationally engaged to the battery 38.

The second connectors 102 are complementary to the first connectors 100 and thus are positioned to engage the first connectors 100, upon threaded engagement of the upper cap 54 to the tube 18, to operationally engage the solar panel 98 to the battery 38.

A scale 104 is engaged to the lower cap 56 and is operationally engaged to the microprocessor 40 upon threaded engagement of the lower cap 56 to the bottom 58 of the tube 18. The scale 104 is configured to determine of a mass of the unit of the prescription item that is dispensed through the orifice 22. The scale 104 also serves to indicate to the microprocessor 40 that the prescription item is positioned in the lower chamber 26, thereby enabling the microprocessor to cease additional dispensing of the prescription item until the already dispensed dose has been removed.

A pair of first contacts 106 is engaged to the lower cap 56 and is operationally engaged to the scale 104. A pair of second contacts 108 is engaged to the tube 18 and is operationally engaged to the microprocessor 40. The second contacts 108 are complementary to the first contacts 106 and thus are positioned to engage the first contacts 106, upon threaded engagement of the lower cap 56 to the tube 18, to operationally engage the scale 104 to the microprocessor 40.

A GPS transceiver 110 is engaged to the tube 18 and is positioned in the lower chamber 26. The GPS transceiver 110 is operationally engaged to the microprocessor 40 and is Global Positioning System enabled. The GPS transceiver 110 is configured to receive the coordinates of the tube 18 and to relay the coordinates to an electronic device, thus allowing tracking of the tube 18.

A communications transceiver 112 is engaged to the tube 18 and is positioned in the lower chamber 26. The communications transceiver 112 is operationally engaged to the microprocessor 40 and is configured to communicate with an electronic device. The communications transceiver 112 can be used to enter programming into the microprocessor 40. The device 10 also may comprise a speaker 114 and a microphone 116, which are operationally engaged to the microprocessor 40 and thereby enable two way communication with the user. The speaker 114 also can serve to provide an audio signal for indicating dosing time.

In use, a sleeve 34 having a suitable arrangement of panels 60 positioned therein is positioned in the upper chamber 24 by the pharmacist. The pharmacist then positions the prescription items in the compartments 62 and programs the microprocessor 40 with a dosing regimen. The upper cap 54 and lower cap 56 are affixed to the tube 18 to secure the prescription items therein, and the device is ready to be handed to the user. The units of the prescription items are dispensed to the user, upon authentication and at prescribed intervals, for collection from the lower chamber 26 via the aperture 32.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. A prescription item dispensing device comprising:
   a tube;
   a cap selectively lockable to a top of the tube for closing the tube; and
   a mounting plate engaged to and positioned within the tube defining upper and lower chambers, the mounting plate having an orifice positioned therein, the tube having an aperture positioned therein and opening into the lower chamber;
   a sleeve selectively positionable in the upper chamber such that a lower end of the sleeve is aligned with the orifice, wherein the sleeve is configured for positioning of a prescription item;
   first and second doors engaged to the tube and the mounting plate, respectively, and being configured for selectively closing the aperture and the orifice, respectively, the first and second doors being selectively linear actuator actuated; and
   an authenticator engaged to the tube and being configured for authenticating an identity of a user, wherein the authenticator is configured for authenticating the identity of the user, positioning the first and second doors for actuated opening for dispensing a unit of the prescription item into the lower chamber for retrieval by the user via the aperture.

2. The prescription item dispensing device of claim 1, further including a battery and a microprocessor engaged to the tube and positioned in the lower chamber, the microprocessor being operationally engaged to the battery.

3. The prescription item dispensing device of claim 2, further including:
   the cap being threadedly couplable to the tube, the cap having a pinhole extending thereinto proximate to a perimeter thereof; and
   a locking linear actuator positioned within a wall of the tube proximate to the top, the locking linear actuator being operationally engaged to the microprocessor, such that the microprocessor is positioned for selectively actuating the locking linear actuator for inserting a piston of the locking linear actuator into the pinhole, thereby preventing rotation of the cap for locking the cap to the tube.

4. The prescription item dispensing device of claim 2, further including the cap comprising an upper cap selectively lockable to the top and a lower cap selectively lockable to a bottom of the tube.

5. The prescription item dispensing device of claim 1, further including a gasket engaged to the cap and being configured for sealably engaging the tube as the cap is threadedly engaged to the tube.

6. The prescription item dispensing device of claim 2, further including:
   a plurality of panels engaged to and positioned in the sleeve such that the panels define a plurality of compartments within the sleeve, each compartment having an associated opening at the lower end of the sleeve; and
   the second door being one of a set of second doors, each second door being positioned for selectively closing an associated orifice of a set of orifices, the associated orifice being aligned with an opening of a respective compartment of the sleeve positioned in the upper chamber.

7. The prescription item dispensing device of claim 6, further including the set of second doors comprising from one to six second doors.

8. The prescription item dispensing device of claim 2, further including the authenticator comprising at least one of:
   a display engaged to an outer surface of the tube and being operationally engaged to the microprocessor, the display being touch enabled and configured for presenting a pin entry box, wherein the microprocessor is configured for verifying the identity of the user or of a pharmacist upon successful entry of a pin code, for dispensing and filling purposes, respectively;
   a fingerprint scanner engaged to the tube and being operationally engaged to the microprocessor, wherein the microprocessor is configured for authenticating fingerprints for verifying the identity of the user or the pharmacist; and
   a camera engaged to the outer surface of the tube and being operationally engaged to the microprocessor, wherein the camera is configured for capturing a facial or ocular image of the user or the pharmacist, enabling the microprocessor for performing facial or iris recognition for verifying the identity of the user or the pharmacist.

9. The prescription item dispensing device of claim 8, further including the display being configured for displaying one or more of a time, a date, user information, and prescription information.

10. The prescription item dispensing device of claim 8, further including a sensor engaged to the outer surface of the tube and being operationally engaged to the microprocessor, the sensor being configured for detecting motion proximate to the tube and for signaling the microprocessor thereof, positioning the microprocessor for selectively actuating the display, the fingerprint scanner, and the camera.

11. The prescription item dispensing device of claim 6, further including:
   a motor engaged to the mounting plate and operationally engaged to the microprocessor, such that the microprocessor is positioned for selectively actuating the motor, the lower end of the sleeve being gearedly engageable to a shaft of the motor, such that the motor is positioned for rotating the sleeve within the upper chamber for selectively aligning a respective opening with a respective orifice in the mounting plate;
   a pickup plate selectively insertable into the upper chamber and gearedly engageable to the shaft of the motor, the pickup plate having a set of first voids positioned therein; and
   a plurality of inserts selectively engageable to the pickup plate such that each first void has a respective insert positioned thereover, each insert having a second void positioned therethrough, the second void having a respective profile, such that the plurality of inserts comprises inserts having second voids of a variety of profiles, such that the second insert is selectively engageable to the pickup plate for reprofiling a respective second void, wherein the respective void is configured for positioning of the unit of the prescription item.

12. The prescription item dispensing device of claim 11, further including a spring bearing engaged to the cap, the shaft of the motor extending through a channel in the sleeve defined by the plurality of panels, such that the shaft is positioned for engaging the spring bearing.

13. The prescription item dispensing device of claim 1, further including a chute engaged to the mounting plate and extending from the orifice into the lower chamber, wherein the chute is configured for directing the unit of the prescription item from the sleeve into the lower chamber.

14. The prescription item dispensing device of claim 2, further including:
   the battery being rechargeable; and
   a port engaged to the outer surface of the tube and being operationally engaged to the battery and the microprocessor, wherein the port is configured for insertion of a plug of a power cord for operationally engaging the battery to a source of electrical current for charging the battery, and wherein the port is configured for engaging a plug of a communications cord for operationally engaging the microprocessor to an electronic device for enabling programming of the microprocessor.

15. The prescription item dispensing device of claim 4, further including:
   the battery being rechargeable;
   a solar panel engaged to the upper cap and being operationally engaged to the battery, wherein the solar panel is configured for converting electromagnetic radiation to an electrical current for charging the battery;
   a pair of first connectors engaged to the upper cap and being operationally engaged to the solar panel; and
   a pair of second connectors engaged to the tube and being operationally engaged to the battery, the second connectors being complementary to the first connectors, such that the second connectors are positioned for engaging the first connectors upon threaded engagement of the upper cap to the tube, for operationally engaging the solar panel to the battery.

16. The prescription item dispensing device of claim 4, further including:
   a scale engaged to the lower cap and being operationally engaged to the microprocessor upon threaded engagement of the lower cap to the bottom of the tube, wherein the scale is configured for determining of a mass of the unit of the prescription item dispensed through the orifice;
   a pair of first contacts engaged to the lower cap and being operationally engaged to the scale; and
   a pair of second contacts engaged to the tube and being operationally engaged to the microprocessor, the second contacts being complementary to the first contacts, such that the second contacts are positioned for engaging the first contacts upon threaded engagement of the lower cap to the tube, for operationally engaging the scale to the microprocessor.

17. The prescription item dispensing device of claim 2, further including a GPS transceiver engaged to the tube and positioned in the lower chamber, the GPS transceiver being operationally engaged to the microprocessor, the GPS transceiver being Global Positioning System enabled, wherein the GPS transceiver is configured for receiving the coordinates of the tube and for relaying the coordinates to an electronic device.

18. The prescription item dispensing device of claim 2, further including a communications transceiver engaged to the tube and positioned in the lower chamber, the communications transceiver being operationally engaged to the microprocessor, wherein the communications transceiver is configured for communicating with an electronic device.

19. A prescription item dispensing device comprising:
a tube;
a battery engaged to the tube and positioned in the lower chamber, the battery being rechargeable;
a microprocessor engaged to the tube and positioned in the lower chamber, the microprocessor being operationally engaged to the battery;
a cap selectively lockable to a top of the tube for closing the tube, the cap being threadedly couplable to the tube, the cap having a pinhole extending thereinto proximate to a perimeter thereof, the cap comprising an upper cap selectively lockable to the top and a lower cap selectively lockable to a bottom of the tube;
a locking linear actuator positioned within a wall of the tube proximate to the top, the locking linear actuator being operationally engaged to the microprocessor, such that the microprocessor is positioned for selectively actuating the locking linear actuator for inserting a piston of the locking linear actuator into the pinhole, thereby preventing rotation of the cap for locking the cap to the tube;
a gasket engaged to the cap and being configured for sealably engaging the tube as the cap is threadedly engaged to the tube;
a mounting plate engaged to and positioned within the tube defining upper and lower chambers, the mounting plate having an orifice positioned therein, the tube having an aperture positioned therein and opening into the lower chamber;
a sleeve selectively positionable in the upper chamber such that a lower end of the sleeve is aligned with the orifice, wherein the sleeve is configured for positioning of a prescription item;
a plurality of panels engaged to and positioned in the sleeve such that the panels define a plurality of compartments within the sleeve, each compartment having an associated opening at the lower end of the sleeve;
first and second doors engaged to the tube and the mounting plate, respectively, and being configured for selectively closing the aperture and the orifice, respectively, the first and second doors being selectively linear actuator actuated, the second door being one of a set of second doors, each second door being positioned for selectively closing an associated orifice of a set of orifices, the associated orifice being aligned with an opening of a respective compartment of the sleeve positioned in the upper chamber, the set of second doors comprising from one to six second doors;
an authenticator engaged to the tube and being configured for authenticating an identity of a user, wherein the authenticator is configured for authenticating the identity of the user, positioning the first and second doors for actuated opening for dispensing a unit of the prescription item into the lower chamber for retrieval by the user via the aperture, the authenticator comprising at least one of:
a display engaged to an outer surface of the tube and being operationally engaged to the microprocessor, the display being touch enabled and configured for presenting a pin entry box, wherein the microprocessor is configured for verifying the identity of the user or of a pharmacist upon successful entry of a pin code, for dispensing and filling purposes, respectively, the display being configured for displaying one or more of a time, a date, user information, and prescription information,
a fingerprint scanner engaged to the tube and being operationally engaged to the microprocessor, wherein the microprocessor is configured for authenticating fingerprints for verifying the identity of the user or the pharmacist, and
a camera engaged to the outer surface of the tube and being operationally engaged to the microprocessor, wherein the camera is configured for capturing a facial or ocular image of the user or the pharmacist, enabling the microprocessor for performing facial or iris recognition for verifying the identity of the user or the pharmacist;
a sensor engaged to the outer surface of the tube and being operationally engaged to the microprocessor, the sensor being configured for detecting motion proximate to the tube and for signaling the microprocessor thereof, positioning the microprocessor for selectively actuating the display, the fingerprint scanner, and the camera;
a motor engaged to the mounting plate and operationally engaged to the microprocessor, such that the microprocessor is positioned for selectively actuating the motor, the lower end of the sleeve being gearedly engageable to a shaft of the motor, such that the motor is positioned for rotating the sleeve within the upper chamber for selectively aligning a respective opening with a respective orifice in the mounting plate;
a pickup plate selectively insertable into the upper chamber and gearedly engageable to the shaft of the motor, the pickup plate having a set of first voids positioned therein;
a plurality of inserts selectively engageable to the pickup plate such that each first void has a respective insert positioned thereover, each insert having a second void positioned therethrough, the second void having a respective profile, such that the plurality of inserts comprises inserts having second voids of a variety of profiles, such that the second insert is selectively engageable to the pickup plate for reprofiling a respective second void, wherein the respective void is configured for positioning of the unit of the prescription item;
a spring bearing engaged to the cap, the shaft of the motor extending through a channel in the sleeve defined by the plurality of panels, such that the shaft is positioned for engaging the spring bearing;
a chute engaged to the mounting plate and extending from the orifice into the lower chamber, wherein the chute is configured for directing the unit of the prescription item from the sleeve into the lower chamber;
a port engaged to the outer surface of the tube and being operationally engaged to the battery and the microprocessor, wherein the port is configured for insertion of a plug of a power cord for operationally engaging the battery to a source of electrical current for charging the battery, and wherein the port is configured for engaging a plug of a communications cord for operationally engaging the microprocessor to an electronic device for enabling programming of the microprocessor;

- a solar panel engaged to the upper cap and being operationally engaged to the battery, wherein the solar panel is configured for converting electromagnetic radiation to an electrical current for charging the battery;
- a pair of first connectors engaged to the upper cap and being operationally engaged to the solar panel;
- a pair of second connectors engaged to the tube and being operationally engaged to the battery, the second connectors being complementary to the first connectors, such that the second connectors are positioned for engaging the first connectors upon threaded engagement of the upper cap to the tube, for operationally engaging the solar panel to the battery;
- a scale engaged to the lower cap and being operationally engaged to the microprocessor upon threaded engagement of the lower cap to the bottom of the tube, wherein the scale is configured for determining of a mass of the unit of the prescription item dispensed through the orifice;
- a pair of first contacts engaged to the lower cap and being operationally engaged to the scale;
- a pair of second contacts engaged to the tube and being operationally engaged to the microprocessor, the second contacts being complementary to the first contacts, such that the second contacts are positioned for engaging the first contacts upon threaded engagement of the lower cap to the tube, for operationally engaging the scale to the microprocessor;
- a GPS transceiver engaged to the tube and positioned in the lower chamber, the GPS transceiver being operationally engaged to the microprocessor, the GPS transceiver being Global Positioning System enabled, wherein the GPS transceiver is configured for receiving the coordinates of the tube and for relaying the coordinates to an electronic device; and
- a communications transceiver engaged to the tube and positioned in the lower chamber, the communications transceiver being operationally engaged to the microprocessor, wherein the communications transceiver is configured for communicating with an electronic device.

* * * * *